United States Patent
Johnson et al.

(12) 
(10) Patent No.: US 6,187,808 B1
(45) Date of Patent: Feb. 13, 2001

(54) HEXAHYDRO-NAPHTHALENONE OXIMES AND HYDRAZONES

(75) Inventors: Stephen Joseph Johnson; Leonard Theodore Meltzer; Lawrence David Wise, all of Ann Arbor, MI (US)

(73) Assignee: Warner-Lambert Company, Morris Plains, NJ (US)

(*) Notice: Under 35 U.S.C. 154(b), the term of this patent shall be extended for 0 days.

(21) Appl. No.: 09/402,046
(22) PCT Filed: Jun. 2, 1999
(86) PCT No.: PCT/US99/12271
  § 371 Date: Sep. 27, 1999
  § 102(e) Date: Sep. 27, 1999
(87) PCT Pub. No.: WO00/06536
  PCT Pub. Date: Feb. 10, 2000

Related U.S. Application Data

(60) Provisional application No. 60/094,392, filed on Jul. 28, 1998.

(51) Int. Cl.[7] .......... A61K 31/15; A61K 31/381; C07C 251/34; C07C 251/74; C07D 333/02
(52) U.S. Cl. .......... 514/438; 514/639; 514/640; 514/641; 549/74; 564/251; 564/253; 564/256
(58) Field of Search .......... 514/438, 639, 514/640, 641; 549/74; 564/253, 251, 256

(56) References Cited

U.S. PATENT DOCUMENTS 5,369,120   11/1994   Woodruff et al. .......... 514/409

FOREIGN PATENT DOCUMENTS 0 077 754   4/1983   (EP) .

OTHER PUBLICATIONS

Suzuki, Akira, et al., *Bulletin of the chemicalsociety of Japan*, "Delta 9(10)–Octal–1–One and Its Molecular Compound", 1962, vol. 35, pp. 2027–2031.

*Primary Examiner*—Joseph K. McKane
*Assistant Examiner*—Taofiq A. Solola
(74) *Attorney, Agent, or Firm*—Charles W. Ashbrook

(57) ABSTRACT

This invention provides 6-amino-3,4,5,6,7,8-hexahydro-2H-naphthalen-1-one oximes and hydrazones which are useful in treating Parkinson's disease.

13 Claims, No Drawings

HEXAHYDRO-NAPHTHALENONE OXIMES AND HYDRAZONES

This application is a 371 of PCT/US99/12271 Jun. 2, 1999 and claims the benefit of Prov. Appln. Ser. No. 60/094, 392 Jul. 28, 1998.

FIELD OF THE INVENTION

This invention provides 6-amino-3,4,5,6,7,8-hexahydro-2H-naphthalen-1-one oximes and hydrazones which are useful in treating Parkinson's disease.

BACKGROUND OF THE INVENTION

Parkinson's disease is a degenerative disorder caused by the loss of dopaminergic neurons in the part of the brain that controls motor function. The disease is characterized by progressive motor dysfunction, cognitive disability, and death. Conventional treatments employ 3-hydroxy-L-tyrosine, commonly referred to as levodopa or L-DOPA. L-DOPA is a precursor in the natural production of dopamine, and it enhances levels of dopamine in the central nervous system. Unfortunately, L-DOPA loses its efficacy after prolonged use, presumably because of the continued degeneration of the neurons that convert it to dopamine. Prolonged treatment generally requires the use of additional dopaminergic agonists be used in combination with L-DOPA. Typical agents commonly utilized in adjunctive therapy with L-DOPA include pergolide and bromocryptine. Such agents often cause undesirable side-effects such as adverse cardiac effects, increased states of confusion and hallucinations, and exacerbation of pre-existing dyskinesia.

The need continues to find new agents that are useful to treat Parkinson's disease. Ideally, an agent will replace the use of L-DOPA completely, and be sufficiently effective and safe such that adjunctive therapy with additional drugs is obviated. We have now discovered a series of oxime and hydrazone derivatives of a naphthalenone which exhibit good in vivo agonist activity at both the D1 and the D2 dopamine receptors. The compounds are thus useful for treating Parkinson's disease.

SUMMARY OF THE INVENTION

This invention provides 6-amino-3,4,5,6,7,8-hexahydro-2H-naphthalen-1-one oximes and hydrazones having Formula I

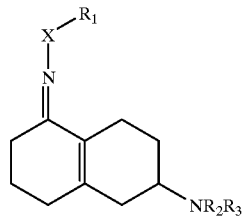

wherein:
R$_1$ is hydrogen, C$_{1-C6}$ alkyl, (CH$_2$)$_n$ phenyl, or (CH$_2$)$_n$-substituted phenyl;
R$_2$ is hydrogen, C$_1$–C$_6$ alkyl, (CH$_2$)$_n$ phenyl, (CH$_2$)$_n$-substituted phenyl, or (CH)$_n$-thienyl;
R$_3$ is hydrogen or C$_1$–C$_6$ alkyl;
X is O or N;
n is 1, 2, or 3; and the pharmaceutically acceptable acid addition salts thereof.

In a preferred embodiment, R$_2$ and R$_3$ both are lower alkyl, especially propyl.

Especially preferred compounds are the oximes of Formula 1, where X is O. Within this group, R$_1$ is preferably hydrogen or lower alkyl such as methyl, ethyl, or propyl.

Particularly preferred compounds of this invention include the following:

(±)-6-Dipropylamino-3,4,5,6,7,8-hexahydro-2H-naphthalen-1-one;
6-Dipropylamino-3,4,5,6,7,8-hexahydro-2H-naphthalen-1-one oxime;
6-Dipropylamino-3,4,5,6,7,8-hexahydro-2H-naphthalen-1-one O-methyl oxime;
6-amino-3,4,5,6,7,8-hexahydro-2H-naphthalen-1-one oxime;
6-methylamino-3,4,5,6,7,8-hexahydro-2H-naphthalen-1-one oxime;
6-ethylamino-3,4,5,6,7,8-hexahydro-2H-naphthalen-1-one oxime; 6-n-propylamino-3,4,5,6,7,8-hexahydro-2H-naphthalen-1-one oxime;
6-iso butylamino-3,4,5,6,7,8-hexahydro-2H-naphthalen-1-one oxime;
6-(2-phenylethyl)amino-3,4,5,6,7,8-hexahydro-2H-naphthalen-1-one oxime;
6-(2-(2-thienyl)ethyl)amino-3,4,5,6,7,8-hexahydro-2H-naphthalen-1-one oxime;
6-(N-methyl-N-n-propylamino)-3,4,5,6,7,8-hexahydro-2H-naphthalen-1-one oxime;
6-(N-ethyl-N-isopropylamino)-3,4,5,6,7,8-hexahydro-2H-naphthalen-1-one oxime;
6-(N-n-butyl-N-n-propylamino)-3,4,5,6,7,8-hexahydro-2H-naphthalen-1-one oxime;
6-(N-(2-(2-thienyl)ethyl)-N-propylamino)-3,4,5,6,7,8-hexahydro-2H-naphthalen-1-one oxime;
6-(N-(2-phenylethyl)-N-propylamino)-3,4,5,6,7,8-hexahydro-2H-naphthalen-1-one oxime;
6-dimethylamino-3,4,5,6,7,8-hexahydro-2H-naphthalen-1-one oxime;
6-diethylamino-3,4,5,6,7,8-hexahydro-2H-naphthalen-1-one oxime;
6-di-n-butylamino-3,4,5,6,7,8-hexahydro-2H-naphthalen-1-one oxime;
6-di(2-phenylethyl)amino-3,4,5,6,7,8-hexahydro-2H-naphthalen-1-one oxime;
6-di(2-(2-thienyl)ethyl)amino-3,4,5,6,7,8-hexahydro-2H-naphthalen-1-one oxime;
6-amino-3,4,5,6,7,8-hexahydro-2H-naphthalen-1-one O-methyl oxime;
6-methylamino-3,4,5,6,7,8-hexahydro-2H-naphthalen-1-one O-methyl oxime;
6-ethylamino-3,4,5,6,7,8-hexahydro-2H-naphthalen-1-one O-methyl oxime;
6-n-propylamino-3,4,5,6,7,8-hexahydro-2H-naphthalen-1-one O-methyl oxime;
6-tert-butylamino-3,4,5,6,7,8-hexahydro-2H-naphthalen-1-one O-methyl oxime;
6-(2-phenylethyl)amino-3,4,5,6,7,8-hexahydro-2H-naphthalen-1-one O-methyl oxime;
6-(2-(2-thienyl)ethyl)amino-3,4,5,6,7,8-hexahydro-2H-naphthalen-1-one O-methyl oxime;
6-(N-methyl-N-n-propylamino)-3,4,5,6,7,8-hexahydro-2H-naphthalen-1-one O-methyl oxime;

6-(N-ethyl-N-n-propylamino)-3,4,5,6,7,8-hexahydro-2H-naphthalen-1-one O-methyl oxime;

6-(N-n-butyl-N-n-propylamino)-3,4,5,6,7,8-hexahydro-2H-naphthalen-1-one O-methyl oxime;

6-(N-(2-(2-thienyl)ethyl)-N-isopropylamino)-3,4,5,6,7,8-hexahydro-2H-naphthalen-1-one O-methyl oxime;

6-(N-(2-phenylethyl)-N-n-propylamino)-3,4,5,6,7,8-hexahydro-2H-naphthalen-1-one O-methyl oxime;

6-dimethylamino-3,4,5,6,7,8-hexahydro-2H-naphthalen-1-one O-methyl oxime;

6-diethylamino-3,4,5,6,7,8-hexahydro-2H-naphthalen-1-one O-methyl oxime;

6-di-n-butylamino-3,4,5,6,7,8-hexahydro-2H-naphthalen-1-one O-methyl oxime;

6-di(2-phenylethyl)amino-3,4,5,6,7,8-hexahydro-2H-naphthalen-1-one O-methyl oxime;

6-di(2-(2-thienyl)ethyl)amino-3,4,5,6,7,8-hexahydro-2H-naphthalen-1-one O-methyl oxime;

6-di-n-propylamino-3,4,5,6,7,8-hexahydro-2H-naphthalen-1-one O-ethyl oxime;

6-diisopropylamino-3,4,5,6,7,8-hexahydro-2H-naphthalen-1-one O-propyl oxime;

6-di-n-propylamino-3,4,5,6,7,8-hexahydro-2H-naphthalen-1-one O-butyl oxime;

6-diisopropylamino-3,4,5,6,7,8-hexahydro-2H-naphthalen-1-one O-pentyl oxime;

6-n-dipropylamino-3,4,5,6,7,8-hexahydro-2H-naphthalen-1-one O-hexyl oxime;

6-di-n-propylamino-3,4,5,6,7,8-hexahydro-2H-naphthalen-1-one O-phenyl oxime;

6-di-n-propylamino-3,4,5,6,7,8-hexahydro-2H-naphthalen-1-one O-benzyl oxime;

6-di-n-propylamino-3,4,5,6,7,8-hexahydro-2H-naphthalen-1-one O-phenethyl oxime;

6-di-n-propylamino-3,4,5,6,7,8-hexahydro-2H-naphthalen-1-one hydrazone;

6-di-n-propylamino-3,4,5,6,7,8-hexahydro-2H-naphthalen-1-one N-methylhydrazone; and 6-di-n-propylamino-3,4,5,6,7,8-hexahydro-2H-naphthalen-1-one N,N-dimethylhydrazone.

The invention additionally provides a pharmaceutical formulation comprising a compound of Formula I admixed with a pharmaceutically acceptable diluent, excipient, or carrier thereof.

Another embodiment of this invention is a method for treating Parkinson's disease comprising administering to a human having Parkinson's disease and in need of treatment an effective amount of a compound of Formula I.

DETAILED DESCRIPTION OF THE INVENTION $R_1$ in Formula I includes "$C_1$–$C_6$ alkyl," which term means a straight or branched hydrocarbon moiety having from one to six carbon atoms. Typical of such groups include methyl, ethyl, n-propyl, isopropyl, sec-butyl, tert-butyl, n-pentyl, 1,1-dimethylbutyl, and 1ethylbutyl. The term "$(CH_2)_n$ phenyl" means phenylmethyl, 2-phenylethyl, and 3phenylpropyl. The term "$(CH_2)_n$-substituted phenyl" means the foregoing groups wherein the phenyl is substituted with 1, 2, or 3 groups selected from hydroxy, $C_1$–$C_6$ alkoxy, halo (chloro, fluoro, bromo, or iodo), $C_1$–$C_6$ alkyl, nitro, amino, $C_1$–$C_6$ alkylamino, or di-$C_1$–$C_6$ alkylamino.

$R_2$ in Formula I can be alkyl, alkylphenyl, and alkyl-substituted phenyl, as well as $(CH_2)_n$-thienyl. The latter term means a $C_1$–$C_3$ alkylene group having a terminal thienyl substituent, for example, a 2-thienyl or 3-thienyl group. Typical examples include 3-thienylmethyl, 2-(2-thienyl) ethyl, and 3-(2-thienyl)propyl.

The compounds of Formula I can be prepared from readily available starting materials, utilizing routine synthetic procedures well known to organic chemists. Both the oximes and the hydrazones are preferably prepared from the corresponding hexahydro naphthyl ketone, a compound having the formula

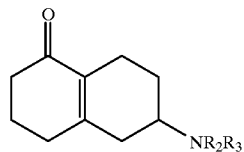

The ketone is readily prepared by reacting 1,3-cyclohexanedione, paraformaldehyde, acetone, and an amine of the Formula $HNR_2R_3$ to form an eneamine, followed by reduction with agents such as sodium cyanoborohydride.

Oximes of Formula I are prepared by reacting the naphthyl ketone with hydroxylamine, alkoxyamine, or a phenoxy or substituted phenoxy amine. The reaction proceeds according to the following scheme:

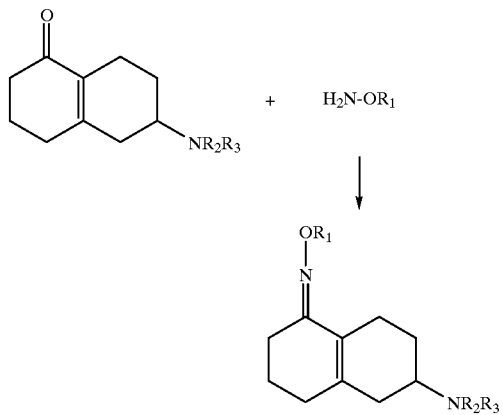

The reaction generally is carried out by mixing the naphthyl ketone with an excess of amine, for instance about 0.1 to about 1.0 molar excess. The reaction is typically carried out in an organic solvent, for example an alcohol such as methanol or ethanol, or an ester such as ethyl acetate or the like. The reaction generally is substantially complete after about 6 to 24 hours when conducted at a temperature of about 10° C. to about 60° C. The product oxime is easily isolated by removing the reaction solvent, and it can be further purified, if desired, by routine methods such as crystallization, chromatography, salt formation, and the like.

The hydrazones of Formula I are prepared by reacting a hydrazine of the formula $H_2N$—$NHR_1$ with the naphthyl ketone. The reaction is depicted by the following scheme:

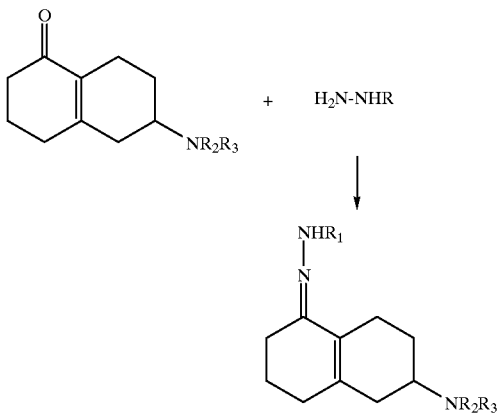

The reaction is carried out in a manner similar to that described above for the oximes; namely, the naphthyl ketone is reacted with an equimolar or slight excess of a hydrazine. The reaction generally is carried out in a solvent such as methanol or ethanol, and typically is complete after about 6 to about 24 hours. The product hydrazone is readily isolated and purified by routine methods.

All of the compounds of Formula I may exist in the form of syn- and anti-isomers by virtue of the imine nitrogen atom. While the anti-isomers are preferred and are normally obtained, the invention includes the individual isomers as well as mixtures of isomers. The individual isomers can be isolated by routine methods such as chromatography over solid supports such as silica gel, or crystallization from solvents such as ethyl acetate, diethyl ether, acetone, and the like.

The invention compounds readily form acid addition salts by reaction with common organic and inorganic acids. Typical acids routinely used to make the pharmaceutically acceptable salts of the invention include hydrochloric and hydrobromic acid, sulfuric acid, phosphoric acid, formic acid, maleic acid, malonic acid, citric acid, hydroxyethyl-sulfonic acid, benzoic acid, and the like.

The synthesis of compounds of Formula I is further illustrated by the following detailed examples which are representative only and are not to be construed as limiting the invention in any respect.

PREPARATION 1
(±)-6-Dipropylamino-3,4,5,6,7,8-hexahydro-2H-naphthalen-1-one 1,3-Cyclohexanedione (22.4 g, 0.2 mol), paraformaldehyde (6.0 g, 0.2 mol), and acetone (15.2 mL, 12 g, 0.2 mol), were stirred in toluene while dipropylamine (27.2 mL, 20.2 g, 0.2 mol) was added rapidly. The solution was heated under reflux through a Dean-Stark water separator for 10 hours. The cooled reaction mixture was washed through a column of silica gel (200 g, 230–400 mesh) with EtOAc. The yellow product containing fractions were combined and concentrated to afford a red-yellow oil (8.0 g) containing the dienaminone. The crude dienaminone (8 g, 34 mmol or less) in MeOH (100 mL) was stirred and cooled on ice water while acetic acid (10 mL) then sodium cyanoborohydride (2.81 g, 44.7 mmol) were added fairly rapidly (Caution: gas evolution). After 10 minutes the cooling bath was removed. After 2.5 hours the bulk of the solvent was removed under vacuum, and the residue was dissolved in water (150 mL). The aqueous solution was washed with Et$_2$O (50 mL), then basified with K$_2$CO$_3$ (20 g), and extracted with Et$_2$O (100 mL, 2×25 mL). The combined extract was dried over MgSO$_4$ and concentrated under vacuum to afford the enone, (±)-6-di-n-propylamino-3,4,5,6,7,8-hexahydro-2H-naphthalen-1-one (4.67 g) as an oil. Analytically pure material was obtained after chromatography (silica gel, EtOAc) and conversion to the hydrochloride salt, mp 145–147° C.

Calculated for C$_{16}$H$_{27}$N$_1$O$_1$.H$_1$Cl$_1$: C, 67.23; H, 9.87; N, 4.9; Cl, 12.4. Found: C, 67.19; H, 10.01; N, 4.88; Cl, 12.66.

EXAMPLES

Example 1
(±)-6-Di-n-propylamino-3,4,5,6,7,8-hexahydro-2H-naphthalen-1-one oxime Hydroxylamine hydrochloride (0.82 g, 11.7 mmol) was added to the ketone (±)-6-di-n-propylamino-3,4,5,6,7,8-hexahydro-2H-naphthalen-1-one (2.02 g, 8.1 mmol) stirred in methanol (14 mL). After 24 hours the solvent was removed under vacuum, the residue was dissolved in water (20 mL), and K$_2$CO$_3$ (1.5 g, 11 mmol) was added. The mixture was extracted with Et$_2$O (50 mL), the extract was dried over MgSO$_4$ and concentrated under vacuum. The residue was dissolved in hot hexanes (80 mL), filtered, then concentrated to 20 mL on a steam bath. The cooled solution left to stand for 2 days and the crystalline solid was separated, washed with hexanes, and vacuum dried to afford (±)-6-dipropylamino-3,4,5,6,7,8-hexahydro-2H-naphthalen-1-one oxime (1.21 g, 56.6% yield), mp 99–102° C. The oxime (1.21 g, 4.59 mmol) in Et$_2$O (50 mL) was treated with a solution of maleic acid (0.58 g, 5 mmol) in Et$_2$O (50 mL). The precipitate was filtered, washed with Et$_2$O, and vacuum dried to afford the maleate salt (1.74 g), mp 164–166° C.

Calculated for: C$_{16}$H$_{28}$N$_2$O$_1$.C$_4$H$_4$O$_4$: C, 63.14; H, 8.48; N, 7.36. Found: C, 62.80; H, 8.56; N, 7.13.

Example 2
(±)6-Di-n-propylamino -3,4,5,6,7,8-hexahydro-2H-naphthalen-1-one O-methyl-oxime Methoxylamine hydrochloride (76 mg, 0.91 mmol) was added to the ketone (±)-6-di-n-propylamino-3,4,5,6,7,8-hexahydro-2H-naphthalen-1-one (172 mg, 0.7 mmol) stirred in methanol (1 mL). After 24 hours the solvent was removed under vacuum, the residue was dissolved in water (2 mL), and K$_2$CO$_3$ (150 mg) was added. The mixture was extracted with Et$_2$O (3×5 mL), the extract was dried over MgSO$_4$ and concentrated under vacuum to afford the crude product, (±)-6-di-n-propylamino-3,4,5,6,7,8-hexahydro-2H-naphthalen-1-one O-methyl-oxime (0.191 g, 99% yield) as an oil. The oil was dissolved in Et$_2$O (5 mL) and treated with HCl in Et$_2$O (1 M, 1 mL, 1 mmol) to afford a solid precipitate. The solid was filtered off, washed with Et$_2$O, and vacuum dried to afford the hydrochloride salt (198 mg, 90% yield), mp 209.5–210° C.

Calculated for C$_{17}$H$_{30}$N$_2$O$_1$.H$_1$Cl$_1$: C, 64/84; H, 9.92; N, 11.26. Found: C, 64.88; H, 10.04; N, 8.82; Cl, 11.09.

Example 3

By following the general procedure of Examples 1 and 2, hydroxylamine hydrochloride was reacted with (±)-6-(N-n-butyl-N-n-propylamino)-3,4,5,6,7,8-hexahydro-2H-naphthalan-1-one to provide the corresponding oxime. The oxime was reacted with one molar equivalent of maleic acid in diethyl ether to give 6-(N-n-butyl-N-n-propylamino)-3,4,5,6,7,8-hexa-hydro-2H-naphthalen-1-one maleate, mp 120–122° C.

Calculated for C$_{17}$H$_{30}$N$_2$O.C$_4$H$_4$O$_4$: C, 93.94; H, 8.69; N, 7.10. Found: C, 93.59; H, 8.50; N, 6.96.

Example 4
(±)-6-Di-n-propylamine-3,4,5,6,7,8-hexahydro-2H-naphthalen-1-one methylhydrazone A solution of 6-di-n-propylamino-3,4,5,6,7,8-hexahydro-2H-naphthalen-1-one (0.52 g, 2.08 mmol) and 1methylhydrazine (0.13 mL, 0.1 g, 2.17 mmol) in 5 mL of methanol was stirred at 24° C. for 4 days. The reaction mixture was concentrated to dryness by evaporation under reduced pressure, and proton NMR indicated the presence of (±)-6-di-n-propylamino-3,4,5,6,7,8-hexahydro-2H-naphthalen-1-one methylhydrazone.

The oximes and hydrazones of Formula I have been evaluated in standard in vitro and in vivo assays which establish their ability to stimulate dopamine receptors in brain tissue. A standard in vivo assay was carried out as follows:

Adult male Sprague-Dawley rats, weight approximately 280 g at surgery are used. Thirty minutes prior to surgery, the rat is injected IP with a mixture of desipramine 25 mg/kg (to protect norepinephrine-containing neurons) and pargyline 25 mg/kg (to potentiate the effect of 6-hydroxydopamine) in sterile saline, injection volume 5 mL/kg. The rat is anesthetized approximately 20 minutes later with chloral hydrate 400 mg/kg IP, (concentration 40 mg/mL to avoid adynamic ileus), the fur on the scalp is clipped, and the rat's head is mounted into a stereotaxic frame. Aseptic surgical technique is maintained. The scalp is cleaned and an incision made sagittally along the midline. The scalp and periosteum are reflected back, and a burr hole made in the skull overlying the medial forebrain bundle (MFB). An injection needle connected to a Hamilton microliter syringe is lowered through the burr hole into the right MFB (posterior 4.8 mm from bregma, lateral 1.1 mm from midline, ventral 8.2 mm from brain surface). 6-Hydroxydopamine HBr, 8 $\mu$g/4 $\mu$L dissolved in sterile saline with 0.1% ascorbic acid, is injected over 5 minutes using an Orion Sage Model 341B syringe pump. The needle is allowed to remain in place 4 minutes after the injection is completed and then removed. The burr hole is sealed with bone wax, and the skin incision closed with wound clips. The rat is placed in a recovery cage, with a heating pad underneath, and allowed to recover from anesthesia before being returned to its home cage. The rat's behavior, food intake, and wound condition is monitored daily following surgery. Any signs of infection or distress will be dealt with in accordance with advice from LAR. The wound clips are removed 7 to 10 days postsurgery. Lesioned animals appear behaviorally normal, unless given dopamine (DA) agonists.

Following a 3-week period for recovery and for the development of DA receptor supersensitivity in the lesioned side of the brain, the rat is taken from its home cage, weighed, and connected to an automated rotation counting apparatus (RotoRat, MED Associates). The rat has a fabric harness fastened about its torso, which is connected by a flexible spring to an electromechanical swivel mounted in an overhead frame. The rat is placed in a large steel bowl (47 cm top diameter) in which it may move freely below the swivel. The bowl is surrounded by and opaque barrier to isolate the rat from its surroundings. Movements of the rat in clockwise and counterclockwise directions are counted and recorded on-line by computer. Experimental sessions last from 1 to 12 hours, with 3 to 6 hours being typical. Following the experiment, the rat is returned to its home cage.

At the first postsurgery session, each rat is dosed with apomorphine 50 $\mu$g/kg SC. This drug is a direct acting DA agonist and will induce contraversive (away from the lesioned side) rotation in lesioned rats. This movement is counterclockwise in rats lesioned in the right MFB. Any rats not exhibiting at least 100 contraversive rotations in the hour following apomorphine injection are regarded as having an incomplete lesion and are removed from further use and euthanized.

The following Table 1 presents the results of three compounds evaluated in the foregoing assay. The reference compound is 5-hydroxy-2-(N,N-dipropyl)-aminotetralin (5-HODPAT), a known DA agonist. Representative invention compounds evaluated were 6-di-n-propylamine-3,4,5,6,7,8-hexahydro-2H-naphthalen-1-one oxime (Compound A, the compound of Example 1) and 6-di-n-propylamino-3,4,5,6,7,8-hexahydro-2H-naphthalen-1-one O-methyl oxime (Compound B, the compound of Example 2).

All compounds were administered orally (PO). Full contraversive rotations were counted and are recorded for each 30-minute interval.

TABLE I

| Minutes Post-Administration | Oral | | | | |
|---|---|---|---|---|---|
| | Compound A | | Compound B | | 5-HoDPAT |
| | 1 mg | 3 mg | 1 mg | 3 mg | 1 mg |
| 30.000 | 37.000 | 173.00 | 51.000 | 163.00 | 178.00 |
| 60.000 | 124.00 | 281.00 | 223.00 | 327.00 | 328.00 |
| 90.000 | 224.00 | 350.00 | 330.00 | 282.00 | 350.00 |
| 120.00 | 312.00 | 338.00 | 361.00 | 271.00 | 381.00 |
| 150.00 | 332.00 | 329.00 | 334.00 | 261.00 | 378.00 |
| 180.00 | 280.00 | 301.00 | 318.00 | 299.00 | 363.00 |
| 210.00 | 268.00 | 292.00 | 336.00 | 320.00 | 301.00 |
| 240.00 | 285.00 | 301.00 | 286.00 | 312.00 | 252.00 |
| 270.00 | 278.00 | 291.00 | 294.00 | 289.00 | 268.00 |
| 300.00 | 295.00 | 298.00 | 304.00 | 312.00 | 194.00 |
| 330.00 | 298.00 | 289.00 | 294.00 | 326.00 | 211.00 |
| 360.00 | 288.00 | 297.00 | 230.00 | 341.00 | 165.00 |
| 390.00 | 296.00 | 277.00 | 226.00 | 341.00 | 151.00 |
| 420.00 | 246.00 | 282.00 | 250.00 | 330.00 | 158.00 |
| 450.00 | 276.00 | 288.00 | 221.00 | 329.00 | 144.00 |
| 480.00 | 221.00 | 310.00 | 247.00 | 353.00 | 146.00 |
| 510.00 | 180.00 | 280.00 | 221.00 | 375.00 | 143.00 |
| 540.00 | 158.00 | 269.00 | 223.00 | 325.00 | 132.00 |
| 570.00 | 105.00 | 277.00 | 218.00 | 327.00 | 135.00 |
| 600.00 | 118.00 | 274.00 | 181.00 | 321.00 | 80.00 |
| 630.00 | 96.000 | 241.00 | 140.00 | 30.00 | 101.00 |
| 660.00 | 106.00 | 240.00 | 79.000 | 294.00 | 74.00 |
| 690.00 | 73.000 | 252.00 | 73.000 | 278.00 | 52.00 |
| 720.00 | 42.000 | 238.00 | 61.000 | 288.00 | 55.00 |

Another assay utilized to measure DA agonist activity of the invention compounds involves examining their ability to alter the increase in L-DOPA synthesis and the inhibition of L-DOPA decarboxylase caused by gamma-butyrolactone (GBL), 3-hydroxybenzylhydrazine HCl (NSD 1015). GBL causes an increase in L-DOPA synthesis in rat corpus striatum and mesolimbic regions of brain tissue. NSD 1015 slows the metabolism of L-DOPA. Compounds that reverse this increase in L-DOPA levels are antagonists at presynaptic dopamine receptors.

Male Long-Evans rats (200–250 g) from Blue Spruce Farms (Altamont, N.Y.) were used for the assay. Animals had free access to laboratory chow and tap water, and were housed four to a cage in a temperature-controlled room with a 12/12 hour light/dark schedule. Rats were killed by decapitation. The brain was rapidly removed and placed on an ice-cooled plate for dissection of different brain regions, ie, corpus striatum and mesolimbic regions. Tissue samples were 15 frozen on dry ice and stored at −20° C. until assayed for DOPA. DOPA levels were determined by high pressure liquid chromatography with electrochemical detection.

Invention compounds were administered by oral gavage 1 hour before sacrifice. GBL and NSD 1015 were administered 30 minutes before sacrifice (750 mg/kg IP and 100 mg/kg IP, respectively). One group (n=4) of animals received no treatments. They exhibited a baseline L-DOPA level of 1.25 µg/g. A control group receiving GBL and NSD 1015 (but no invention compound had an L-DOPA level of 4.11 µg/g. Table 11 lists the percent by which representative invention compounds reversed the increase in L-DOPA caused by GBL and NSD 1015. Each invention compound was administered by oral gavage at a dose of 3 µg/kg.

TABLE II

| Compound of Example No. | % Reversal in Striatum | % Reversal in Mesolimbic |
|---|---|---|
| 1 | 85 | — |
| 2 | 70 | 56 |
| 3 | 76 | 89 |

The foregoing data establish that the invention compounds act as agonists at presynaptic dopamine receptors in the striatum and mesolimbic regions of the brain.

The compounds of the present invention can be prepared and administered in a wide variety of oral and parenteral dosage forms for the treatment of Parkinson's disease. For instance, the compounds can be administered by injection, that is, intravenously, intramuscularly, intracutaneously, subcutaneously, intraduodenally, or intraperitoneally. Also, the compounds of the present invention can be administered by inhalation, for example, intranasally, as well as transdermally and orally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutics use as agents for the treatment of Parkinson's disease, the compounds utilized in the pharmaceutical method of this invention are administered at a dose that is effective to increase the production of dopamine by brain neurons. The initial dosage of about 1 to about 100 mg per kilogram of body weight daily will be effective. A daily dose range of about 25 to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg.

The following examples illustrate typical formulations provided by the invention.

Example 5

| Tablet Formulation | |
|---|---|
| Ingredient | Amount (mg) |
| Syn-6-N-propyl-N-ethylamino-3,4,5,6,7,8-hexahydro-2H-naphthalen-1-one oxime | 25 |
| Lactose | 50 |
| Corn starch (for mix) | 10 |
| Corn starch (paste) | 10 |
| Magnesium stearate (1%) | 5 |
| Total | 100 |

The naphthyl oxime, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from 1 to 4 times-a-day for treatment of Parkinson's disease.

Example 6

| Preparation for Oral Solution | |
|---|---|
| Ingredient | Amount |
| 6-Di-n-butylamino-3,4,5,6,7,8-hexahydro-2H-naphthalen-1-one O-benzyl oxime hydrobromide | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the naphthyl oxime is dissolved therein. The saccharin, sodium benzoate, flavor, and dye are added and dissolved. The volume is adjusted to 100 mL with distilled water. Each milliliter of syrup contains 4 mg of invention compound.

Example 7
Parenteral Solution

In a solution of 700 mL of propylene glycol and 200 mL of water for injection is suspended 20 g of 6-diethylamino-3,4,5,6,7,8-hexahydro-2H-naphthalen-1-one-N,N-dimethyl-hydrazone maleate. After suspension is complete, the pH is adjusted to 6.5 with 1N sodium hydroxide, and the volume is made up to 1000 mL with water for injection. The formulation is sterilized, filled into 5.0 mL ampoules each containing 2.0 mL, and sealed under nitrogen. As dopamine receptor agonists, the compounds of Formula I are useful as agents for the treatment of Parkinson's disease. The compounds can be utilized alone, or alternatively in combination with other dopamine agonists, for example L-DOPA, pergolide, and bromocrypstine. The invention compounds exhibit a longer duration of action following administration than observed with conventional treatments, and thus are advantageous to the management of patients having Parkinson's disease.

What is claimed is:

1. A compound of the formula

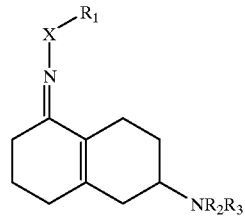

wherein:
   $R_1$ is hydrogen, $C_1$–$C_6$ alkyl, $(CH_2)_n$ phenyl, or $(CH_2)_n$-substituted phenyl;
   $R_2$ is hydrogen, $C_1$–$C_6$ alkyl, $(CH_2)_n$ phenyl, $(CH_2)_n$-substituted phenyl, or $(CH_2)_n$-thienyl;
   $R_3$ is hydrogen or $C_1$–$C_6$ alkyl;
   X is O or N;
   n is 1, 2, or 3;
and the pharmaceutically acceptable acid addition salts thereof.

2. A compound of claim 1 wherein X is N.

3. A compound of claim 1 wherein X is O.

4. A compound of claim 3 wherein $R_2$ and $R_3$ both are $C_1$–$C_6$ alkyl.

5. A compound of claim 4 wherein $R_2$ and $R_3$ both are n-propyl.

6. The compound of claim 5 which is (±)-6-Dipropylamino-3,4,5,6,7,8-hexahydro-2H-naphthalen-1-one oxime.

7. The compound of claim 5 which is (±)-6-Dipropylamino-3,4,5,6,7,8-hexahydro-2H-naphthalen-1-one O-methyl-oxime.

8. A pharmaceutical composition comprising a compound of claim 1 admixed with a pharmaceutically acceptable carrier, diluent, or excipient therefore.

9. A composition of claim 8 employing a compound wherein X is O, $R_2$ and $R_3$ both are n-propyl.

10. A composition of claim 9 wherein in the compound $R_1$ is hydrogen or methyl.

11. A method for treating Parkinson's disease comprising administering to a human having Parkinson's disease and in need of treatment an effective amount of a compound of claim 1.

12. A method according to claim 11 employing a compound wherein X is O and $R_2$ and $R_3$ both are n-propyl.

13. A method according to claim 12 employing a compound wherein $R_1$ is hydrogen or methyl.

* * * * *